(12) United States Patent
Carrascal De Las Heras et al.

(10) Patent No.: US 11,215,840 B2
(45) Date of Patent: Jan. 4, 2022

(54) TESTING A BIOLOGICAL SAMPLE BASED ON SAMPLE SPECTROGRAPHY AND MACHINE LEARNING TECHNIQUES

(71) Applicant: INTERNATIONAL BUSINESS MACHINES CORPORATION, Armonk, NY (US)

(72) Inventors: Ginés Carrascal De Las Heras, Madrid (ES); Sumit Patel, Round Rock, TX (US); David Bacarella, Naperville, IL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 222 days.

(21) Appl. No.: 16/210,446

(22) Filed: Dec. 5, 2018

(65) Prior Publication Data

US 2020/0124868 A1    Apr. 23, 2020

(30) Foreign Application Priority Data

Oct. 18, 2018    (EP) .................................... 18382743

(51) Int. Cl.
   *G02B 27/48*    (2006.01)
   *G01B 11/00*    (2006.01)
   (Continued)

(52) U.S. Cl.
   CPC ............ *G02B 27/48* (2013.01); *G01B 11/002* (2013.01); *G01P 3/366* (2013.01); *G16B 40/00* (2019.02);
   (Continued)

(58) Field of Classification Search
   CPC ........ G16B 40/00; G16B 40/10; G16B 40/20; G16B 40/30; G16B 40/99; G02B 27/48;
   (Continued)

(56) References Cited

U.S. PATENT DOCUMENTS

2004/0070756 A1    4/2004  Rastopov
2005/0228591 A1*  10/2005  Hur ...................... G06K 9/6269
                                                              702/19

(Continued)

OTHER PUBLICATIONS

Moshou, Dimitrios, et al. "Automatic detection of 'yellow rust'in wheat using reflectance measurements and neural networks." Computers and electronics in agriculture 44.3 (2004): 173-188. (Year: 2004).*

(Continued)

*Primary Examiner* — Jesse P Frumkin
(74) *Attorney, Agent, or Firm* — Scott Dobson; Andrew D. Wright; Roberts Calderon Safran & Cole, P.C.

(57) ABSTRACT

A computer-implemented method includes: receiving, by a computing device, data corresponding to a dynamic speckle spectrum image associated with a biological sample; comparing, by the computing device, the dynamic speckle spectrum image with a plurality of training images; classifying, by the computing device, a contaminant present in the biological sample, based on the comparing; and providing, by the computing device, information regarding the classification of the contaminant.

20 Claims, 10 Drawing Sheets

(51) Int. Cl.

| | |
|---|---|
| *G01P 3/36* | (2006.01) |
| *G16H 50/70* | (2018.01) |
| *G16H 30/40* | (2018.01) |
| *G16H 50/20* | (2018.01) |
| *G16H 50/50* | (2018.01) |
| *G16H 80/00* | (2018.01) |
| *G16B 40/00* | (2019.01) |
| *G16B 40/20* | (2019.01) |

(52) U.S. Cl.
CPC ............. *G16B 40/20* (2019.02); *G16H 30/40* (2018.01); *G16H 50/20* (2018.01); *G16H 50/50* (2018.01); *G16H 50/70* (2018.01); *G16H 80/00* (2018.01)

(58) Field of Classification Search
CPC ....... G01B 11/002; G01P 3/366; G16H 50/70; G16H 30/40; G16H 50/20; G16H 50/50; G16H 80/00; G16H 40/63; G16H 20/10; G16H 10/40; G16H 50/30; G06F 19/30; G06F 19/32; G06F 19/34; G06Q 50/22; G06Q 50/24; G01N 29/4481; A61B 5/7267; A61B 5/7264
See application file for complete search history.

(56) References Cited

U.S. PATENT DOCUMENTS

| | | | |
|---|---|---|---|
| 2009/0325210 A1 | 12/2009 | Weichselbaum et al. | |
| 2010/0136611 A1 | 9/2010 | Maurer | |
| 2012/0008838 A1 | 1/2012 | Guyon et al. | |
| 2012/0245473 A1* | 9/2012 | Mycek | G01N 21/6486 600/479 |
| 2017/0138923 A1 | 5/2017 | Park et al. | |
| 2017/0173262 A1 | 6/2017 | Veltz | |
| 2017/0290979 A1 | 10/2017 | Gordon et al. | |
| 2018/0082043 A1 | 3/2018 | Witchey et al. | |
| 2018/0150052 A1* | 5/2018 | Cherian | G06N 3/0454 |
| 2020/0107787 A1* | 4/2020 | Sarkaria | A61B 5/01 |
| 2020/0354667 A1* | 11/2020 | Papermaster | C12M 41/36 |
| 2021/0199643 A1* | 7/2021 | Bharitkar | G01N 33/52 |

OTHER PUBLICATIONS

Yoon et al., "A simple and rapid method for detecting living microorganisms in food using laser speckle decorrelation", https://arxiv.org/abs/1603.07343, Mar. 18, 2016, 6 pages.

Passoni et al., "Probability mapping images in dynamic speckle classification," Applied Optics, vol. 52, No. 4, pp. 726-733, Feb. 1, 2013, 8 pages.

Ramírez-Miquet et al., "Differences in activity profile of bacterial cultures studied by dynamic speckle patterns", Proc. SPIE, vol. 8587, 85871P, SPIE BiOS: Imaging, Manipulation, and Analysis of Biomolecules, Cells, and Tissues XI, 2013, 9 pages.

Pra et al., "Dynamic speckle image segmentation using Self-Organizing Maps", Journal of Optics, 18(8):085606, Aug. 2016, 15 pages.

Huang et al., "Low-cost compact diffuse speckle contrast flowmeter using small laser diode and bare charge-coupled-device", https://www.ncbi.nlm.nih.gov/pmc/articles/PMC4975738/#!po=22.3404; Journal of Biomedical Optics 2016, Aug. 8, 2016, 5 pages.

Vega et al., "System of acquisition and processing of images of dynamic speckle", https://www.researchgate.net/publication/273312472_System_of_acquisition_and_processing_of_images_of_dynamic_speckle, VII International Congress of Engineering Physics, Journal of Physics: Conference Series 582, 2015, 9 pages.

Shibata et al., "Development of the portable blood flow measurement system using Laser Speckle Flowgraphy", https://www.researchgate.net/publication/261244511_Development_of_the_portable_blood_flow_measurement_system_using_Laser_Speckle_Flowgraphy/amp, Optical Review 22(2): 955-958, Oct. 2013, 4 pages.

Anonymous, "Outbreaks: Investigation, Response & Evaluation", https://www.fda.gov/food/recallsoutbreaksemergencies/outbreaks/ucm374327.htm, FDA gov, accessed Oct. 2, 2018, 2 pages.

Mell et al., "The NIST Definition of Cloud Computing", NIST, Special Publication 800-145, Sep. 2011, 7 pages.

* cited by examiner

TESTING A BIOLOGICAL SAMPLE BASED ON SAMPLE SPECTROGRAPHY AND MACHINE LEARNING TECHNIQUES

BACKGROUND

The present invention generally relates to sample testing and, more particularly, to sample testing based on the sample's spectrography (referred to herein as dynamic speckle spectrum) and machine learning techniques.

Laboratory and culture testing techniques are used to test biological samples for the presence of contaminants, such as bacteria, mold, viruses, etc. Testing of biological samples may involve the use of dip sticks, chemical reaction analysis, culture mediums, and/or other laboratory equipment and facilities.

SUMMARY

In an aspect of the invention, a computer-implemented method includes: receiving, by a computing device, data corresponding to a dynamic speckle spectrum image associated with a biological sample; comparing, by the computing device, the dynamic speckle spectrum image with a plurality of training images; classifying, by the computing device, a contaminant present in the biological sample, based on the comparing; and providing, by the computing device, information regarding the classification of the contaminant.

In an aspect of the invention, there is a computer program product including a computer readable storage medium having program instructions embodied therewith. The program instructions are executable by a sampling device to cause the computing device to: perform a speckle analysis on a biological sample; and provide data from the speckle analysis to a server device to cause the server device to: classify a contaminant present within the biological sample by comparing a dynamic speckle spectrum image associated with the speckle analysis with a plurality of training images, and provide information regarding the classification of the contaminant.

In an aspect of the invention, a system includes: a portable sampling apparatus having: a housing, a laser diode, a compartment for a vial containing a sample, a charge-couple device (CCD) array, an amplifier, and a processing and communications component. In embodiments, the laser diode is configured to produce a laser beam passing through the sample, the CCD array is configured to detect a speckle pattern produced by the laser beam after passing through the sample, the amplifier is configured to amplify the speckle pattern, and the processing and communications component is configured to process and transmit information regarding the speckle pattern.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

Figure 1:
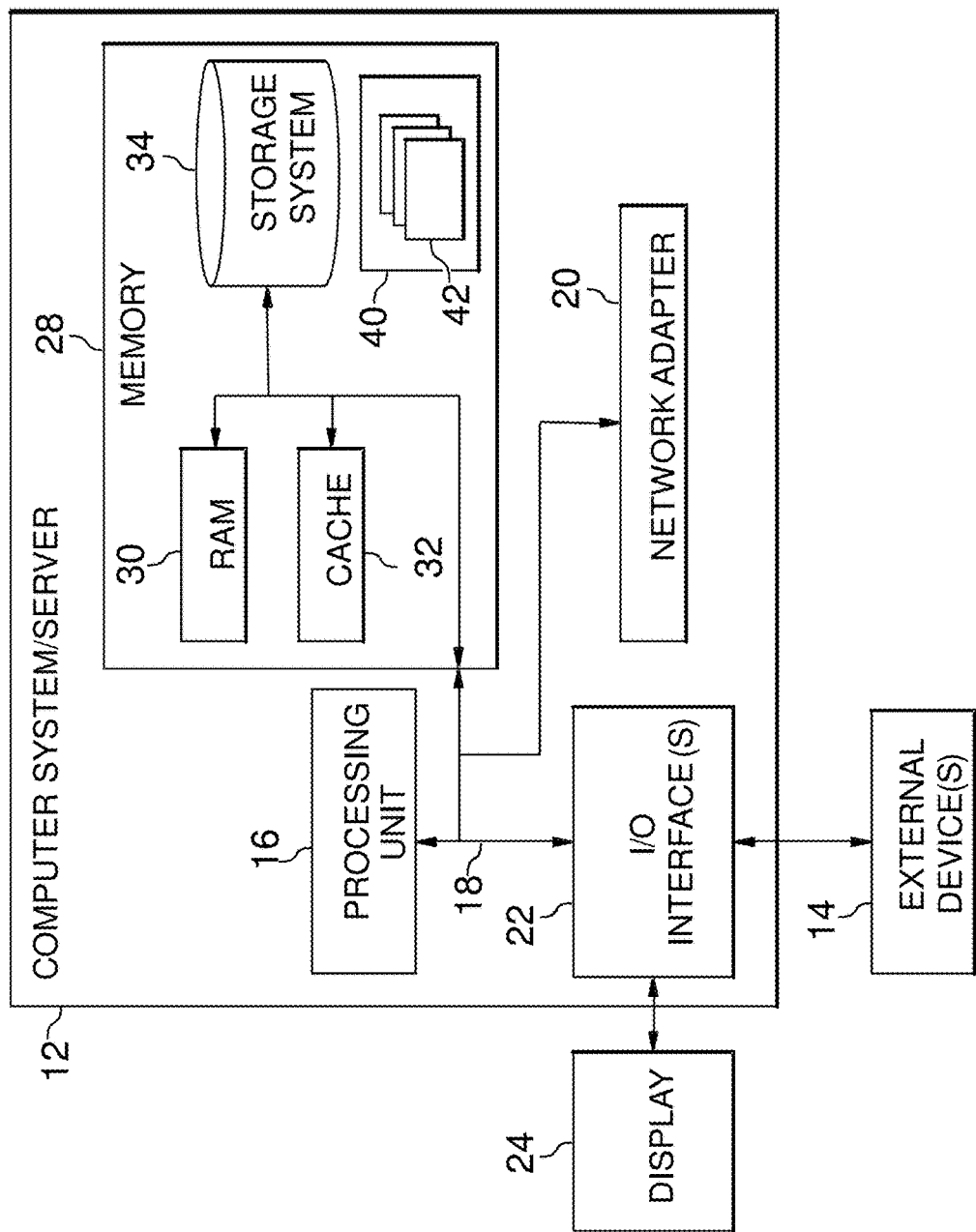
FIG. 1 depicts a cloud computing node according to an embodiment of the present invention.

The present invention generally relates to sample testing and, more particularly, to sample testing based on a sample's dynamic speckle spectrum and machine learning techniques. Bacteria and culture testing for medical and scientific purposes faces accessibility and cost issues requiring expensive, specialized devices and, in many cases, retesting due to poor sample tracking. Aspects of the present invention address such shortfall using a sample testing and analysis system having a pattern identifier capable of communicating with a remote computing server.

In embodiments, aspects of the present invention perform a speckle analysis on a sample (e.g., a liquid biological sample) using a laser diode to obtain the sample's dynamic speckle spectrum via the pattern identifier. More specifically, aspects of the present invention include a system having a portable hardware sampling apparatus in communication with a remote server. As described herein, the sampling apparatus includes a laser diode that outputs a beam of light through the sample, whereby the light scatters across the sample to produce a dynamic speckle spectrum (also referred to herein as a speckle pattern). The speckle pattern is captured by a pattern identifier (e.g., a linear charge-coupled device (CCD) array) implemented within the sampling apparatus. A "squared image" or temporal image of the speckle pattern evolution (e.g., a dynamic speckle spectrum image) over a short period of time is obtained.

As described herein, in embodiments, the laser diode outputs a beam of light with one wavelength (e.g., one color), in order for the light to create an interference pattern (e.g., a speckle pattern) that changes in time. The changes in an image contain information of spatial and temporal frequencies of the interference, however, these frequencies are not wavelengths. Aspects of the present invention apply a Fourier Transform to obtain a representation of the spectrum of these frequencies to create the "squared image" or temporal image of the speckle pattern evolution (e.g., the dynamic speckle spectrum image).

In embodiments, this image is provided to the remote server (e.g., using Internet of Things (IoT) devices and other related communications hardware) and compared with trained classifier images in a computer-based library to automatically identify regularities from the image.

In embodiments, the regularities indicate that a contaminant (e.g., bacteria, virus, etc.) is present in the sample and the classification/type of contaminant (e.g., the species of the contaminant, the concentration level of the contaminant, etc.) based on comparing a sampled image with trained classifier images. As an illustrative example, during a training process, a speckle analysis is performed of sample having a known contaminant (e.g., bacteria type A). Aspects of the present invention store the dynamic speckle spectrum image of the speckle analysis of sample with bacteria type A to classify samples as such that have a matching dynamic speckle spectrum.

As an illustrative example, aspects of the present invention are used to test for contaminants in liquids, such as a water supply. Additionally, or alternatively, aspects of the present invention are used for medical testing (e.g., urine analysis), food contamination testing (e.g., in juices, bottled sauces, etc.). Additionally, or alternatively, aspects of the present invention are used to identify contaminants in air (e.g., using laser/light sources that have properties such that the light scatters when exposed to air and form speckle patterns).

As described herein, aspects of the present invention classify a contaminant based on the sample's dynamic speckle spectrum obtained using the sampling apparatus of the present invention. Additionally, aspects of the present invention classify a contaminant based on metadata associated with the sample. For example, aspects of the present invention use metadata to assist with the classification, such sample collection time of day, geographic location of collection, and/or environment conditions at the time of collection (e.g., weather, temperature, humidity, etc.).

As samples are analyzed and/or as automated results are determined using the trained classifiers, the automated results are saved into a blockchain-based library and a corresponding evidence evolution system to allow for sample comparison and next best action tracking. More specifically, the evidence evolution system includes a library of inputted samples with metadata to enable comparison and evolution of samples as part of a suggested action. In embodiments, the execution of the action can be automated using smart contracts in the blockchain.

As samples are uploaded using the sampling apparatus, pattern identifiers assess the image using pre-programmed identifiers (e.g., Bacteria 1 pattern, Bacteria 2 pattern, etc.) to classify the sample and recommend potential actions (i.e. treat sample with a particular chemical, refer a patient to a medical professional, etc.). Additionally, in example embodiments, users manually input metadata about the sample and compare the metadata to a crowdsourced database to assess samples for which an identifier or recommendations do not currently exists. Also, for bacteria which evolves over time, comparisons can be made such that classification data used to identify the bacteria also evolves using machine learning and cognitive computing techniques. This information and the recommendation actions are saved to a sample management "custody" system leveraging blockchain-like technologies to ensure auditability of sample information (e.g., confirmation that the sample was received when it was dropped off, temperature of sample, etc.). In embodiments, sample management "custody" system includes a system to track and audit metadata associated with samples. In embodiments, automated initialization of process and/or actions is performed using smart contracts (e.g., trigger warning processes, interacting with an IoT-based controller to mitigate treatment of a water supply, trigger physician assignment, etc.).

As described herein, aspects of the present invention include a hardware device that performs machine learning-based speckle analysis on a biological sample with time-series analysis to support testing goals. Also, aspects of the present invention provide an evidence system with phased clear liquid sample evolution that control (e.g., using blockchain technology) how users input test samples and results that are stored, and allowing for sample results to be compared over different time periods and from samples gathered in different geographic locations. As an example, aspects of the present invention provide insight as to how contaminated water samples evolve (e.g., how the speckle pattern evolves over time in response to a treatment).

Aspects of the present invention incorporate a sample management "custody" system using blockchain to ensure that samples and results are linked for accuracy, thus allowing the samples results to be shared quickly and easily. Aspects of the present invention enforce actions based on results (e.g., using smart contracts, communication with IoT-based controllers, communications with computer-based medical provider scheduling systems, etc.). Further, aspects of the present invention incorporate a cloud knowledge base and evidence system with phased sample evolution system to suggest efficient treatments. In embodiments, aspects of the present invention implement a blockchain audit system to ensure sample validity and suggested outcomes as a result of sample evaluation.

In embodiments, aspects of the present invention provide immediate, in situ, results for medical practitioners without the need for costly and wasteful consumables (e.g., dipsticks, culture medium, reactive chemicals, etc.). Additionally, or alternatively, a portable sampling apparatus is used to analyze a sample on-site, without the need to transport the sample to another location (e.g., a laboratory), thus lowering the risk of sample mishandling. Aspects of the present invention provide the capacity to monitor disease evolution on a frequency (e.g., daily) basis to more quickly adjust antibiotics type and dosage for more effective treatment of medical conditions. Aspects of the present invention provide are easy to use in field situations, such as in natural disaster situations, or locations with limited resources. The sample testing apparatus, in accordance with aspects of the present invention, is versatile for testing different types of samples, from drinking water to food samples, leading to the prevention of the spread of diseases. Aspects of the present invention provide more localized results compared to root cause analysis, thereby more effectively preventing the spread of disease. Aspects of the present invention provide automated test results of samples through the use of automatic speckle analysis and communications with a remote server. In embodiments, any variety of colors and wavelengths of source light from laser diodes may be used as part of the speckle analysis on a sample. A network of linked libraries and evidence systems with phased liquid sample evolution are used to create larger sample pools and phased results for better classification and contaminant identification.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
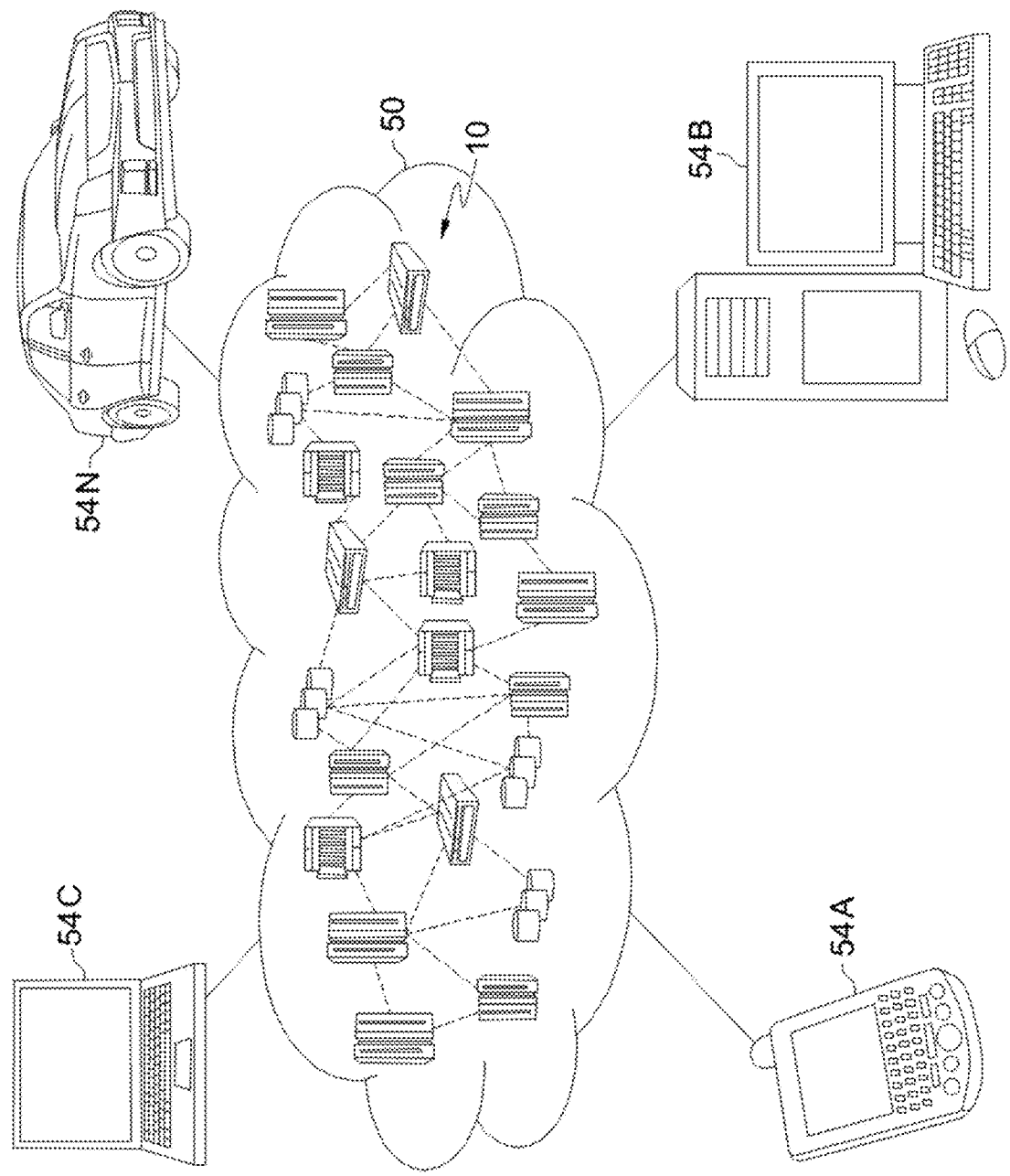
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
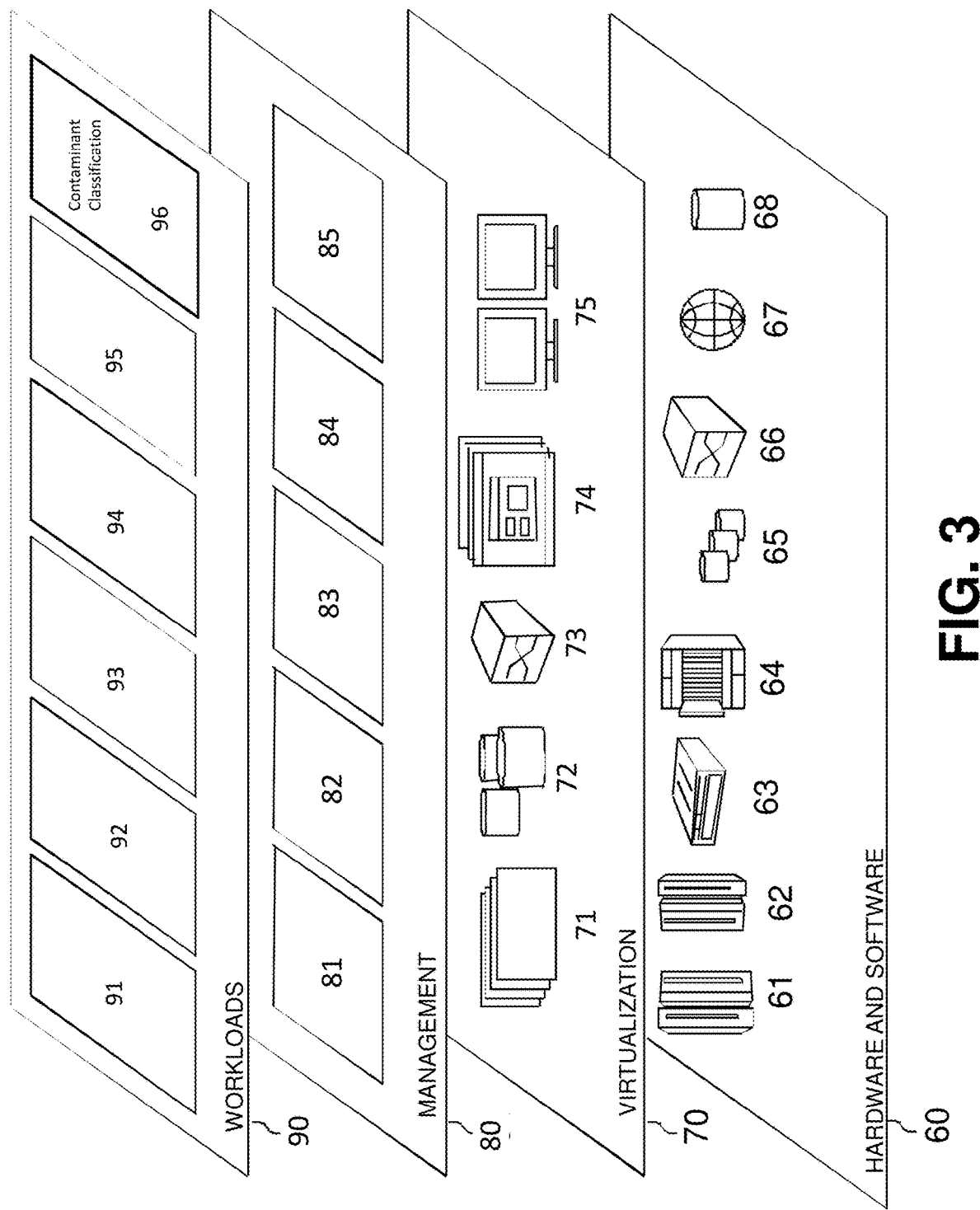
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and contaminant classification 96.

Figure 5:
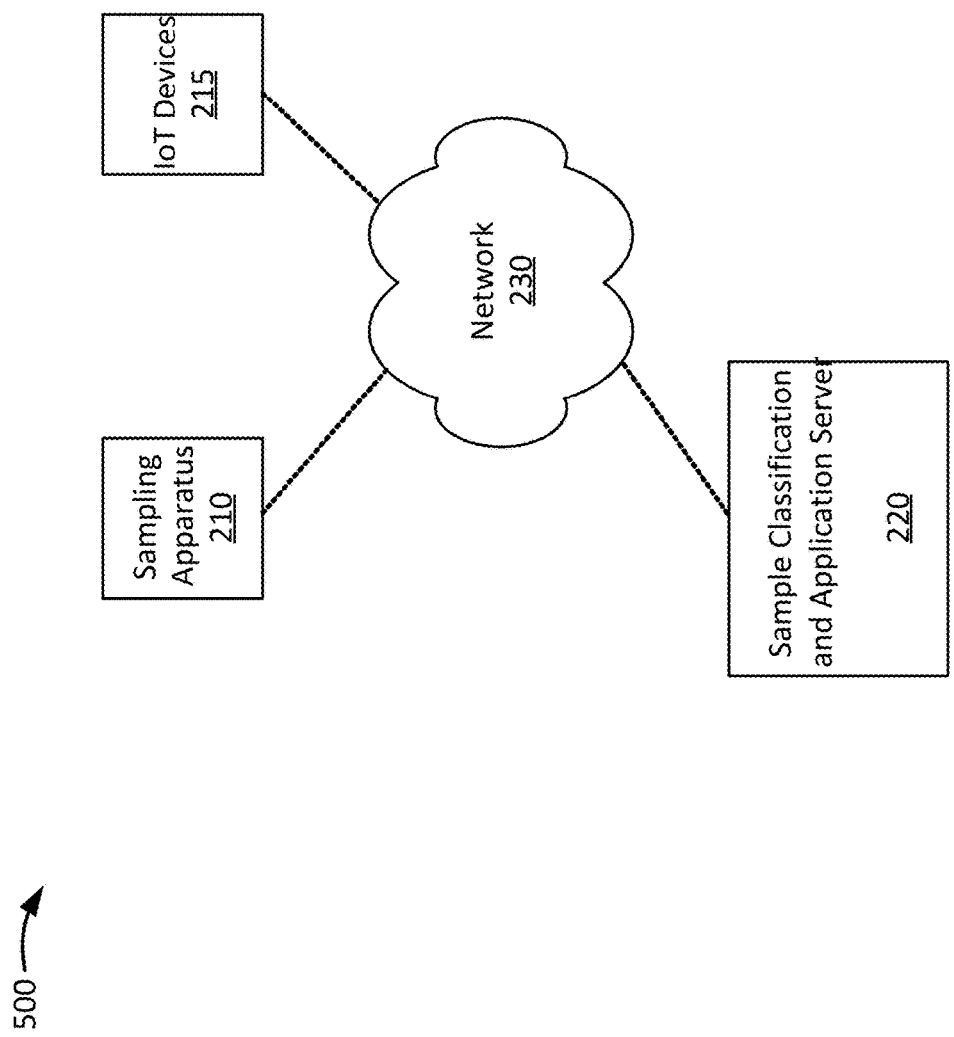
FIG. 5 shows an example environment in accordance with aspects of the present invention.

Referring back to FIG. 1, the program/utility 40 may include one or more program modules 42 that generally carry out the functions and/or methodologies of embodiments of the invention as described herein (e.g., such as the functionality provided by contaminant classification 96). Specifically, the program modules 42 may receive sample dynamic speckle spectrum data from a sampling apparatus, compare sample dynamic speckle spectrum data with training classifier data, classifying the sample based on the matching the dynamic speckle spectrum data with the training classifier data, select and execute a computer-based instruction based on the classification of the sample, storing information regarding the classification, and updating the classification criteria based on previous classification data to aid in future classifications. Other functionalities of the program modules 42 are described further herein such that the program modules 42 are not limited to the functions described above. Moreover, it is noted that some of the modules 42 can be implemented within the infrastructure shown in FIGS. 1-3. For example, the modules 42 may be representative of a sample classification and application server as shown in FIG. 5.

Figure 4A:
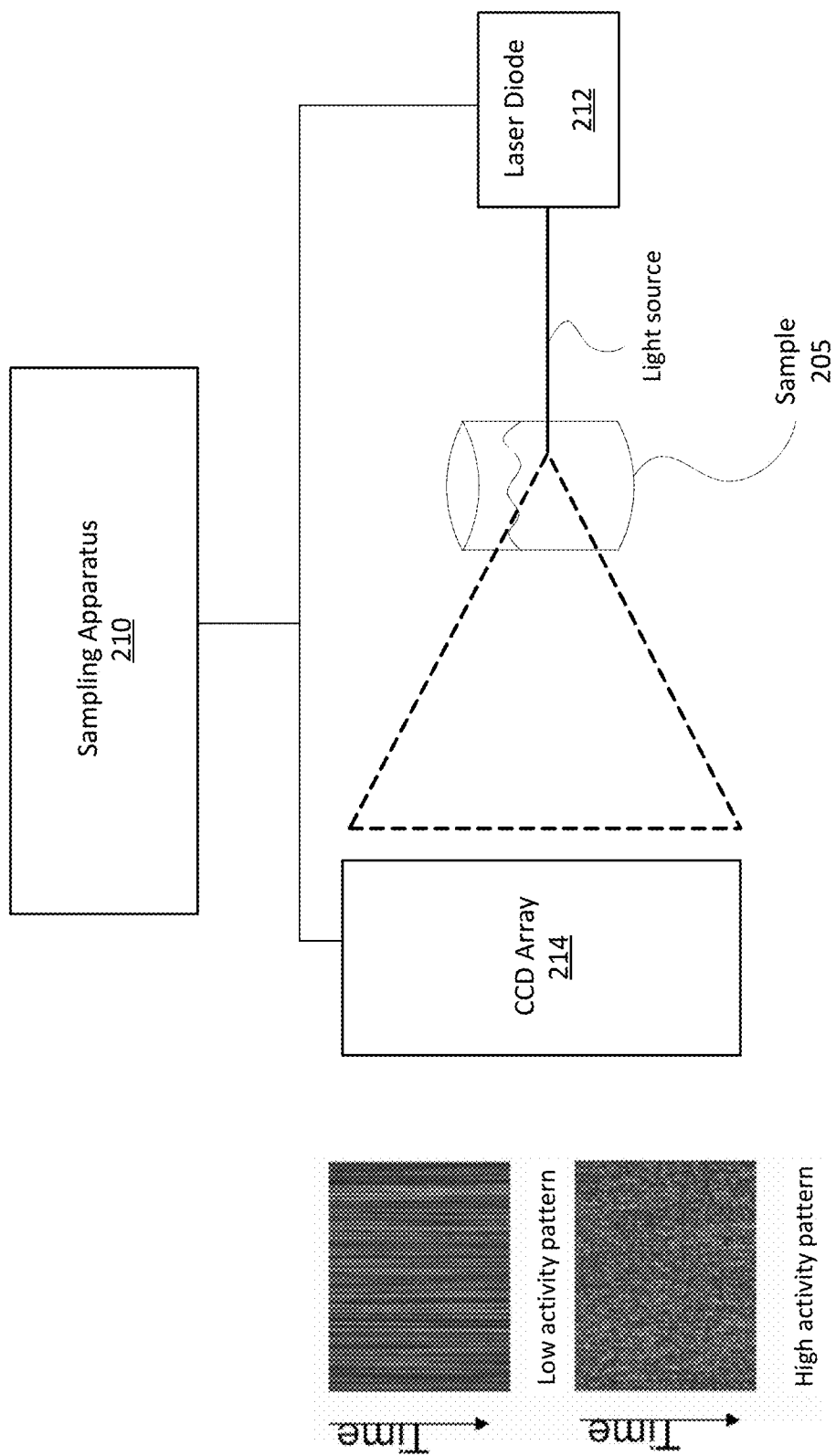
FIGS. 4A and 4B show an overview of an example implementation in accordance with aspects of the present invention.
Figure 4B:
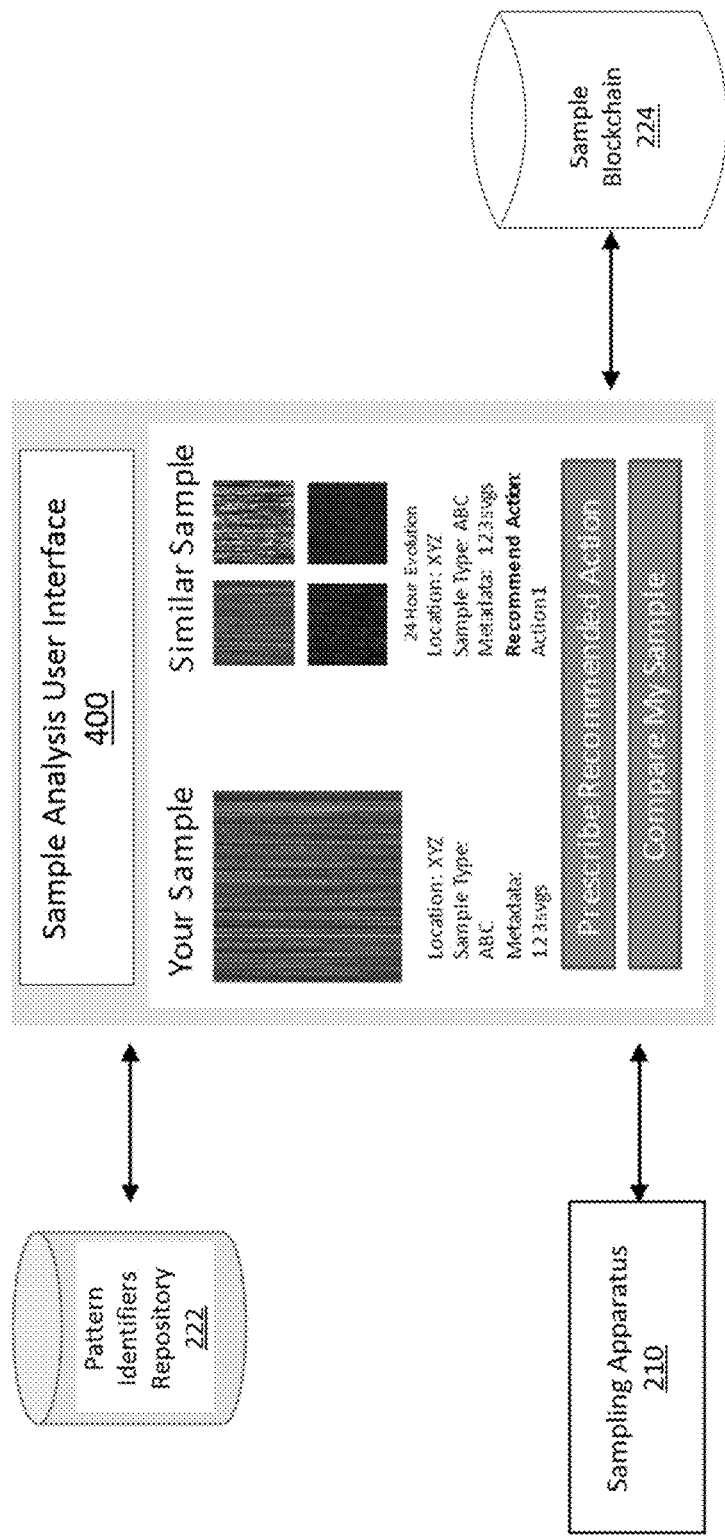

FIGS. 4A and 4B show an overview of an example implementation in accordance with aspects of the present invention. As shown in FIG. 4A, a sampling apparatus 210 includes a laser diode 212 that provides a light source (e.g., a laser beam) that passes through a sample 205 (e.g., a liquid sample in a transparent vial). When the light source passes through the sample 205, the light scatters and produces a dynamic speckle pattern which is detected by a photodiode array (e.g., a CCD array 214) implemented within the sampling apparatus 210. For example, the CCD array 214 takes a composite of several hundred or more images in the time domain to produce the speckle pattern corresponding to the sample's dynamic speckle spectrum. Example high and low activity speckle patterns are shown in FIG. 4A. As described herein, a "high" activity speckle pattern is one in which the number of changes in light patterns (e.g., caused by movements within the liquid) exceeds a threshold, indicating the presence of a contaminant from the movements within the liquid.

As described herein, an image of the speckle pattern is provided by the sampling apparatus 210 to a remote server (e.g., a sample classification and application sever) and compared with other images of other speckle patterns to classify the sample. In embodiments, texture identification of a sample's dynamic speckle spectrum is implemented for classification. In example embodiments, training of Naïve Bayesian Classifier with Fast Fourier Transforms (FFTs) of dynamic speckle images is performed to form trained classifier images. In embodiments, these classifier images are trained with training sample data and tested against actual laboratory results to determine best configuration/classifications. Also, for a given sample, an FFT is applied to the sample's dynamic speckle spectrum to "filter" the sample data for more accurate classification.

Referring to FIG. 4B, an example sample analysis user interface 400 is shown. From the sample analysis user interface 400, options are presented to the user, such as an option to prescribe a recommended action based on the classification, or an option to compare the sample's speckle pattern to other similar sample speckle patterns stored in a repository, such as a pattern identifiers repository 222. In embodiments, details regarding the sample are stored in a sample blockchain 224 to assist in classifications of future samples while maintaining the integrity of the sample data. Additionally, or alternatively, the sample blockchain 224 stores smart contracts and/or other criteria for performing an action based on the details of the sample (e.g., the classification of the sample and/or other metadata associated with the sample).

FIG. 5 shows an example environment in accordance with aspects of the present invention. As shown in FIG. 5, environment 500 includes a sampling apparatus 210, one or more IoT devices 215, a sample classification and application server 220 and a network 230. In embodiments, one or more components in environment 500 may correspond to one or more components in the cloud computing environment of FIG. 2. In embodiments, one or more components in environment 500 may include the components of computer system/server 12 of FIG. 1.

The sampling apparatus 210 includes an apparatus having a housing/casing, a laser diode, a receptacle for setting a vial with a liquid sample a CCD array, an amplifier, and communications hardware for communicating data via the network 230. In embodiments, the sampling apparatus 210 of FIG. 5 corresponds to the example sampling apparatus 210 shown in FIG. 4A. Additional details regarding the sampling apparatus 210 are discussed below with respect to FIG. 6. As described herein, the sampling apparatus 210 performs a speckle analysis on a sample to obtain data regarding the dynamic speckle spectrum of the sample. The sampling apparatus 210 provides the sample dynamic speckle spectrum data to the sample classification and application server 220 for classification purposes. In embodiments, the sampling apparatus 210 forms a dynamic speckle spectrum image of a sample and provides the dynamic speckle spectrum image to the sample classification and application server 220. In alternative embodiments, the sampling apparatus 210 provides raw speckle data of a sample and the sample classification and application server 220 generates the dynamic speckle spectrum image from the raw speckle data.

The IoT device 215 includes one or more sensor devices and/or controller devices capable of communicating via the network 230. For example, in embodiments the IoT device 215 includes a device that controls a water treatment system or food treatment system to treat a water or food supply. As another example, the IoT device 215 includes a control device for treating an air supply (e.g., an HVAC treatment controller). Additionally, or alternatively, the IoT device 215 includes a sensor device that gathers environmental metadata associated with a sample. Additionally, or alternatively, the IoT device 215 includes a location determination device that provides location information of where a sample is collected. In embodiments, one or more IoT devices 215 are implemented within the sampling apparatus 210.

The sample classification and application server 220 includes one or more computing devices (e.g., such as computer system/server 12 of FIG. 1) that receives dynamic speckle spectrum data/speckle pattern data of a sample and classifies the sample based on training data of other speckle patterns. As described herein, the sample classification and application server 220 implements a blockchain for storing and sharing data regarding the results of samples in a secure manner (e.g., to aid in the classification of future samples). In embodiments, the sample classification and application server 220 hosts an application that implements machine learning techniques for updating and refining the classification of future samples as the nature of contaminants evolve. Also, the sample classification and application server 220 hosts an application that performs one or more actions based on the classification of the sample (e.g., controlling an IoT device 215 to treat a water/food/air supply, provide a report or notification regarding the results/classification of a sample, interface with computer-based scheduling systems of a medical professional based on the results/classification of a sample, etc.).

The network 230 may include network nodes, such as network nodes 10 of FIG. 2. Additionally, or alternatively, the network 230 may include one or more wired and/or wireless networks. For example, the network 230 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 230 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks.

The quantity of devices and/or networks in the environment 500 is not limited to what is shown in FIG. 5. In practice, the environment 500 may include additional devices and/or networks; fewer devices and/or networks; different devices and/or networks; or differently arranged devices and/or networks than illustrated in FIG. 5. Also, in some implementations, one or more of the devices of the environment 500 may perform one or more functions described as being performed by another one or more of the devices of the environment 500. Devices of the environment 500 may interconnect via wired connections, wireless connections, or a combination of wired and wireless connections.

Figure 6:
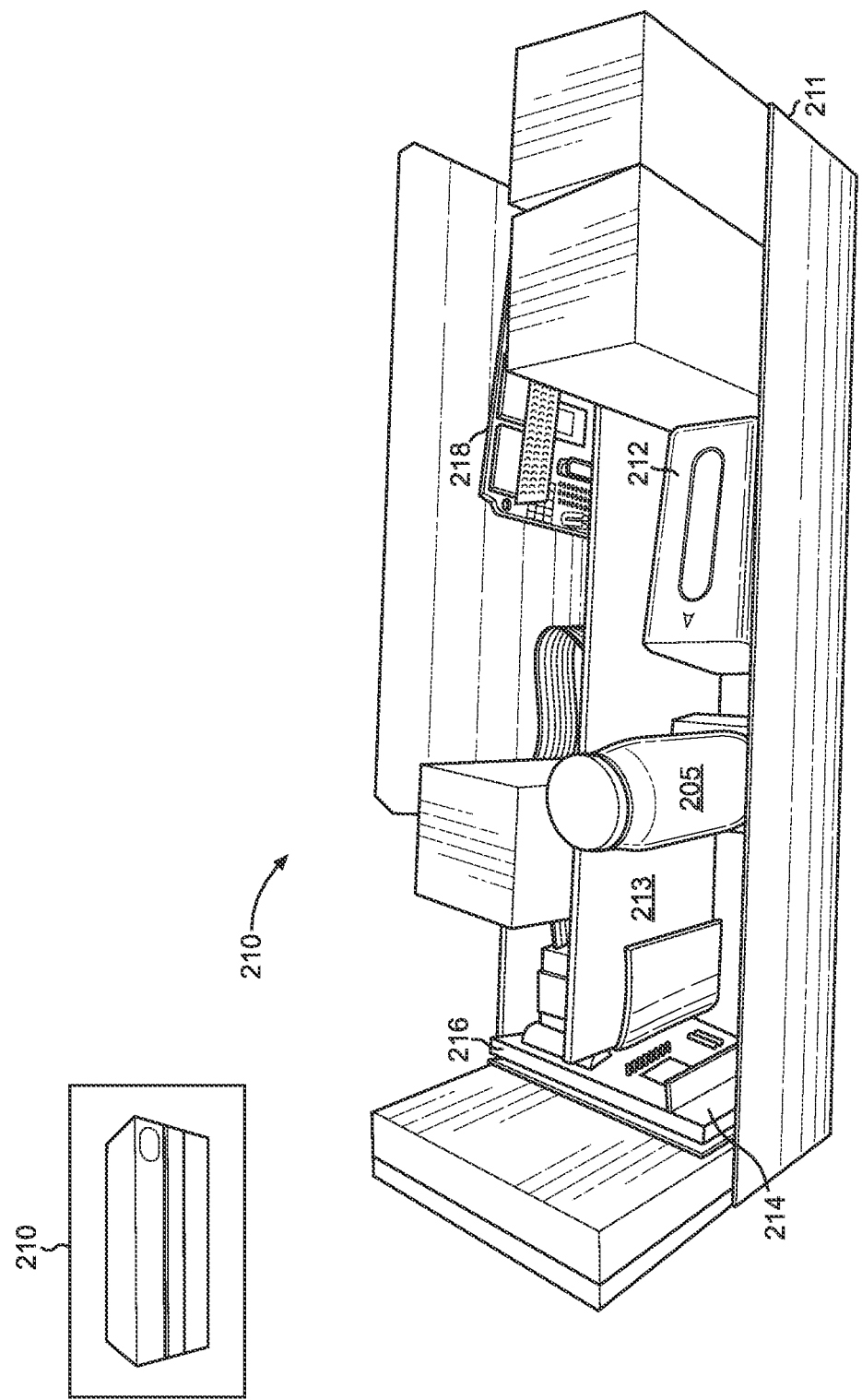
FIG. 6 shows an example sampling apparatus use to collect dynamic speckle spectrum data of a sample in accordance with aspects of the present invention.

FIG. 6 shows an example sampling apparatus use to collect dynamic speckle spectrum data of a sample in accordance with aspects of the present invention. In embodiments, the sampling apparatus 210 is portable such that samples may be analyzed on-site without needing to transport the sample to another location (e.g., a laboratory). As shown in FIG. 6, the sampling apparatus 210 includes a housing 211 (e.g., made of aluminum) with a removable cover to expose interior components of the sampling apparatus 210 and to place a sample 205 within a compartment 213 of the sampling apparatus 210. As shown in the open view of the sampling apparatus 210, the sampling apparatus 210 includes a laser diode 212, a CCD array 214, an amplifier 216, and a processing and communications component 218. As described above with respect to FIG. 4A, the CCD array 214 detects a dynamic speckle pattern (e.g., dynamic speckle spectrum) that is produced when a laser beam from the laser diode 212 passes through the sample 205. In embodiments, the amplifier 216 amplifies the speckle pattern, and the processing and communications component 218, processes the data regarding the speckle pattern to perform a speckle analysis having a dynamic speckle spectrum image, and transmits data regarding the speckle analysis (e.g., to the sample classification and application server 220). Alternatively, the processing and communications component 218 provides raw data from the CCD array 214 (e.g., raw photodetected data) and the sample classification and application server 220 performs the speckle analysis to form a dynamic speckle spectrum image from this raw data. While FIG. 6 shows a particular arrangement of components within the sampling apparatus 210, in practice, the sampling apparatus 210 may include additional components, fewer components, or differently arrange components than the example shown in FIG. 6.

Figure 7:
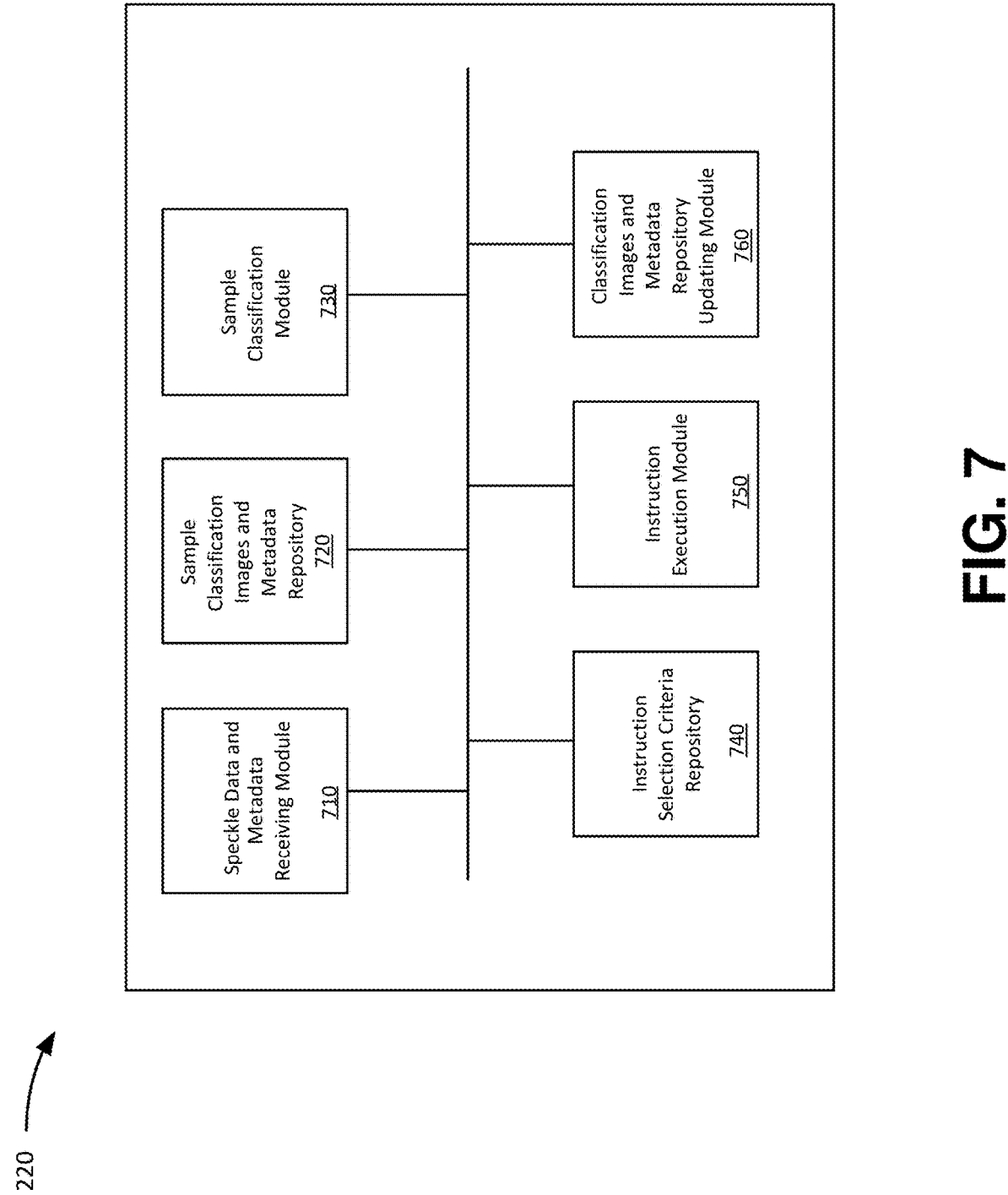
FIG. 7 shows a block diagram of example components of a sample classification and application server in accordance with aspects of the present invention.

FIG. 7 shows a block diagram of example components of a sample classification and application server 220 in accordance with aspects of the present invention. As shown in FIG. 7, the sample classification and application server 220 includes a speckle data and metadata receiving module 710, a sample classification images and metadata repository 720, a sample classification module 730, an instruction selection criteria repository 740, an instruction execution module 750, and a classification images and metadata repository updating module 760. In embodiments, the sample classification and application server 220 may include additional or fewer components than those shown in FIG. 7. In embodiments, separate components may be integrated into a single computing component or module. Additionally, or alternatively, a single component may be implemented as multiple computing components or modules.

The speckle data and metadata receiving module 710 includes a program module (e.g., program module 42 of FIG. 1) that receives dynamic speckle spectrum data of a sample from the sampling apparatus 210. In example embodiments, the speckle data and metadata receiving module 710 applies an FFT function to filter the dynamic speckle spectrum data for more accurate classification. In embodiments, the speckle data and metadata receiving module 710 receives metadata associated with the dynamic speckle spectrum. For example, in embodiments, the speckle data and metadata receiving module 710 receives the metadata from one or more IoT devices 215 associated with or incorporated within the sampling apparatus 210. Example metadata includes location information of where the sample is collected, time/date information from when the sample is collected, environmental condition information associated with the collection of the sample, types of facilities associated with the sample, other IoT devices 215 that control treatment for a supply where the sample originated, etc.). In embodiments, a user may input, via a user interface associated with the sample classification and application server 220, any type of metadata corresponding to details of the sample collection (e.g., the name of the user associated with the sample, information for a medical professional associated with the user, etc.).

The sample classification images and metadata repository 720 includes a data storage device (e.g., storage system 34 of FIG. 1) that stores sample classification training images. More specifically the sample classification images and metadata repository 720 stores training images including dynamic speckle spectrum images (e.g., speckle analysis images) of known contaminant classifications. Further, the sample classification images and metadata repository 720 stores metadata associated with these classification training images. As an illustrative example, during a training process, a speckle analysis is performed of sample having a known contaminant (e.g., bacteria type A). The sample classification images and metadata repository 720 stores the dynamic speckle spectrum image of the speckle analysis of sample with bacteria type A. Further, the sample classification images and metadata repository 720 stores the metadata associated with the dynamic speckle spectrum image, as the dynamic speckle spectrum of bacteria type A may differ under different conditions (e.g., at different times of day, different environmental conditions, different geographic locations, etc.). In example embodiments, the sample classification images and metadata repository 720 is implemented as a blockchain to maintain the integrity and security of the data.

The sample classification module 730 includes a program module (e.g., program module 42 of FIG. 1) that classifies a sample based on sample dynamic speckle spectrum data and metadata received by the speckle data and metadata receiving module 710. In embodiments, the sample classification module 730 classifies the sample by comparing the sample's dynamic speckle spectrum with the sample classification images (e.g., training images) and associated metadata stored by the sample classification images and metadata repository 720. Based on the comparing, the sample classification module 730 determines the classification of the sample by matching the dynamic speckle spectrum data and metadata with the closest sample classification image and associated metadata set. In embodiments, the sample classification module 730 determines candidate matches (e.g., the top three matches, top five matches, etc.). In embodiments, the sample classification module 730 updates a blockchain storing results of sample testing (e.g., information regarding the classification of the sample) to improve and aid in future classifications.

The instruction selection criteria repository 740 includes a program module (e.g., program module 42 of FIG. 1) that stores corresponding instruction criteria to select and execute based on the determined classification of the sample. For example, the instruction selection criteria repository 740 stores criteria that stipulate that an alert or report is generated when any type of contaminant is present in the sample. Additionally, or alternatively, the instruction selection criteria repository 740 stores criteria that stipulate that control instructions should be provided to an IoT device 215 for controlling the treatment operations of a water or air supply controlled by the IoT device 215. Additionally, or alternatively, the instruction selection criteria repository 740 stores criteria that stipulate that a message is sent to a medical provider and/or an appointment is scheduled with the medical provider based on the type/classification of contaminant present in the sample. Additionally, or alternatively, the instruction selection criteria repository 740 stores information regarding smart contracts in a blockchain in which the smart contracts identify actions to perform based on the classification of contaminant present.

The instruction execution module 750 includes a program module (e.g., program module 42 of FIG. 1) that selects an instruction to execute based on the classification of the sample (e.g., as determined by the sample classification module 730) and the criteria stored by the instruction selection criteria repository 740. Once the instruction is selected, the instruction execution module 750 executes the selected instruction. In this way, a mitigating action is performed in response to identifying that a contaminant is present in a sample.

The classification images and metadata repository updating module 760 includes a program module (e.g., program module 42 of FIG. 1) that updates the sample classification images and metadata repository 720. For example, the dynamic speckle spectrum of a contaminant may evolve or change over time, and the classification images and metadata repository updating module 760 tracks these changes and updates the sample classification images and metadata repository 720 accordingly. In embodiments, the classification images and metadata repository updating module 760 tracks the changes in dynamic speckle spectrum of a particular contaminant of a particular classification based on detecting slight deviations between the dynamic speckle spectrum of the contaminant from a current sample, and the stored dynamic speckle spectrum of the contaminant. As described herein, the sample classification module 730 classifies a sample based on the closest match between the dynamic speckle spectrum of a sample and the dynamic speckle spectrum of images stored by the sample classification images and metadata repository 720. However, the specotgraphies may not match completely, and slight deviations may indicate that the behavior of a contaminant is evolving. The classification images and metadata repository updating module 760 tracks these deviations and updates the sample classification images and metadata repository 720 to update the training images as the dynamic speckle spectrum of the contaminant evolves. In this way, the classification images and metadata repository updating module 760 implements machine learning techniques to update the training images such that classifying future samples is accurate as the dynamic speckle spectrum of a contaminant evolves.

Figure 8:
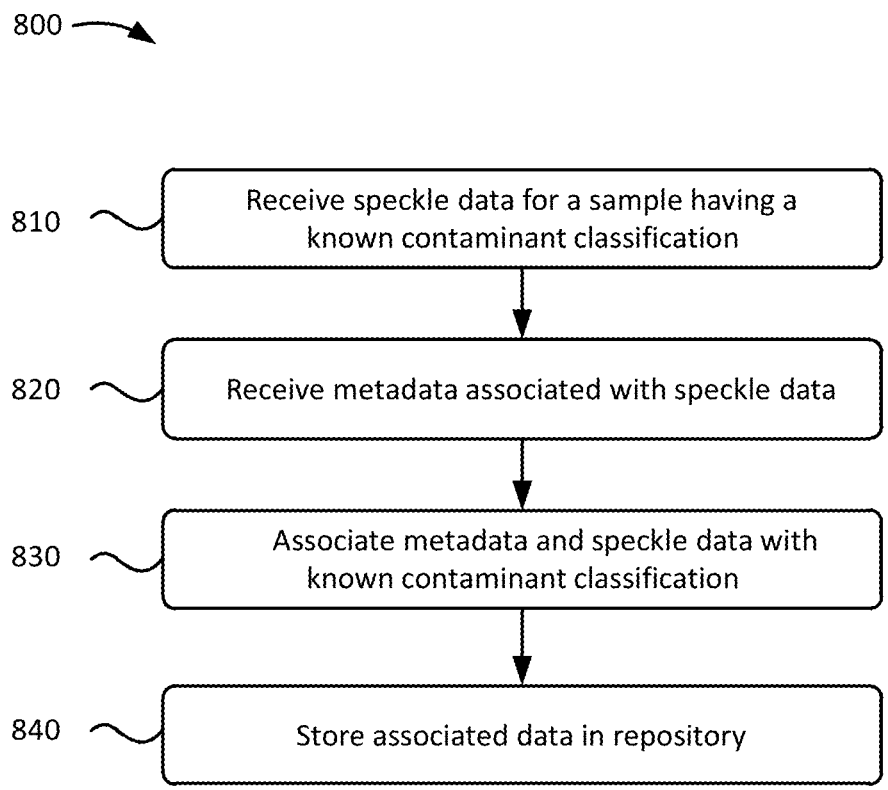
FIG. 8 shows an example flowchart of a process for building a repository of training dynamic speckle spectrum images to be used to classify contaminants present in biological samples in accordance with aspects of the present invention.

FIG. 8 shows an example flowchart of a process for building a repository of training dynamic speckle spectrum images to be used to classify contaminants present in biological samples. The steps of FIG. 8 may be implemented in the environment of FIG. 5, for example, and are described using reference numbers of elements depicted in FIG. 5. As noted above, the flowchart illustrates the architecture, functionality, and operation of possible implementations of systems, methods, and computer program products according to various embodiments of the present invention.

As shown in FIG. 8, process 800 includes receiving speckle data for a sample having a known contaminant (step 810). For example, as described above with respect to the speckle data and metadata receiving module 710, the sample classification and application server 220 receives dynamic speckle spectrum data for a sample having a known contaminant from the sampling apparatus 210. The sample classification and application server 220 receives the dynamic speckle spectrum data as part of an image training process for building pattern identifier images to classify future samples to be tested for contaminants.

Process 800 also includes receiving metadata associated with the speckle data (step 820). For example, as described above with respect to the speckle data and metadata receiving module 710, the sample classification and application server 220 receives metadata associated with the dynamic speckle spectrum data (e.g., time of day of collection, location of collection, etc.).

Process 800 further includes associating the metadata and dynamic speckle spectrum data with the known contaminant classification (step 830). For example, as described above with respect to the sample classification images and metadata repository 720, the sample classification and application server 220 associates the metadata and dynamic speckle spectrum data with the known contaminant classification. In this way, a dataset of dynamic speckle spectrum data and metadata is now associated with a classification of a contaminant for classifying future samples with a matching set of dynamic speckle spectrum and metadata.

Process 800 also includes storing the associated data in a repository (step 840). For example, as described above with respect to the sample classification images and metadata repository 720, the sample classification and application server 220 stores the dataset of dynamic speckle spectrum data and metadata with classification information. In embodiments, the data is stored as training images or a "squared image" of a speckle analysis of the speckle pattern/dynamic speckle spectrum of the known contaminant and the classification of the known contaminant. As described herein the training images and associated metadata is stored in a blockchain to preserve the integrity and security of the stored data.

Figure 9:
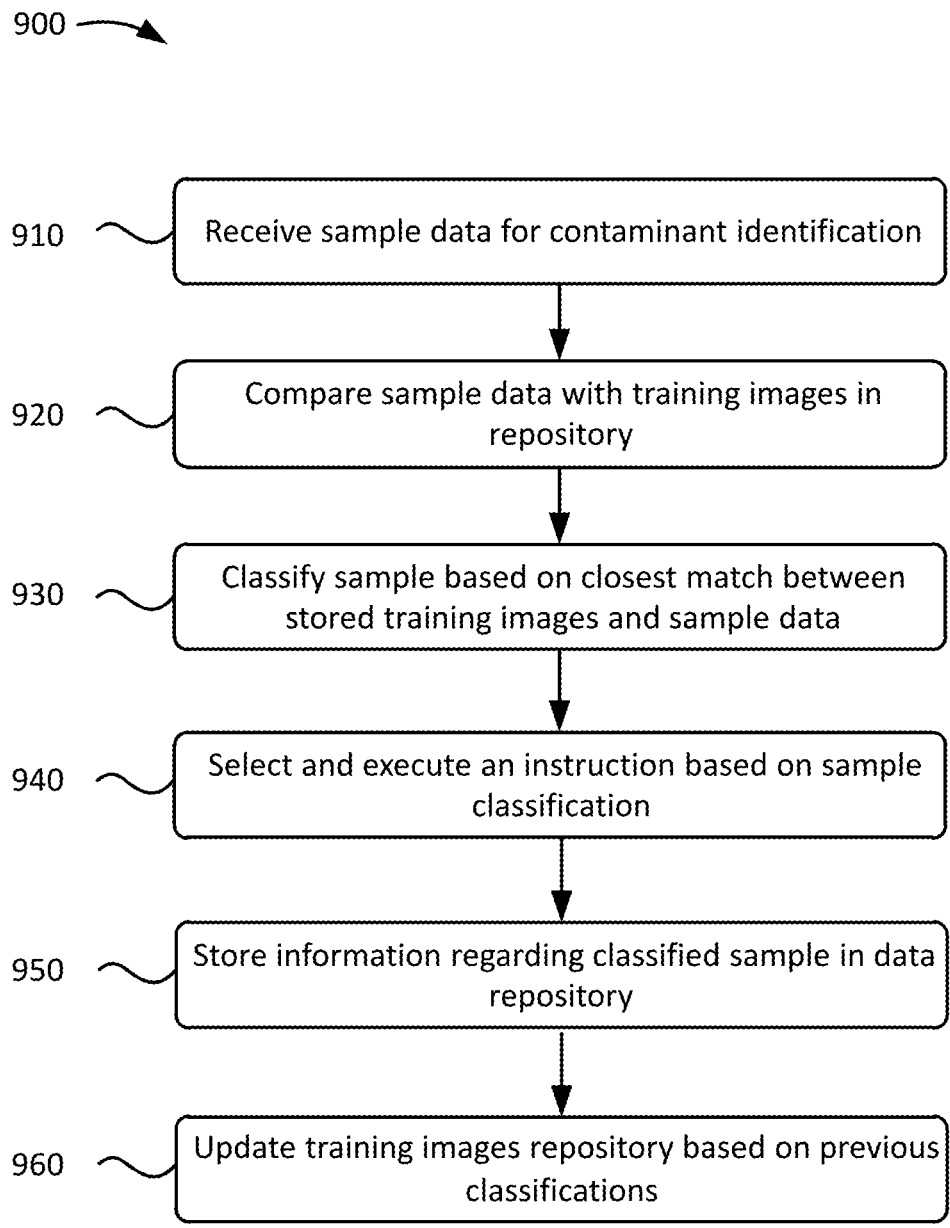
FIG. 9 shows an example flowchart of a process for classifying a sample based on the sample's dynamic speckle spectrum.

FIG. 9 shows an example flowchart of a process for classifying a sample based on the sample's dynamic speckle spectrum. The steps of FIG. 9 may be implemented in the environment of FIG. 5, for example, and are described using reference numbers of elements depicted in FIG. 5. As noted above, the flowchart illustrates the architecture, functionality, and operation of possible implementations of systems, methods, and computer program products according to various embodiments of the present invention.

As shown in FIG. 9, process 900 includes receiving sample data for contamination identification (step 910). For example, as described above with respect to the speckle data and metadata receiving module 710, the sample classification and application server 220 receives sample data, such as an image corresponding to a speckle analysis for the sample, or a dynamic speckle spectrum image associated with the sample (e.g., from the sampling apparatus 210). In embodiments, the sample classification and application server 220 additionally receives metadata associated with the sample.

Process 900 further includes comparing the sample data with training images in a repository (step 920). For example, as described above with respect to the sample classification module 730, the sample classification and application server 220 compares the sample's dynamic speckle spectrum image with the sample classification images (e.g., training images). In embodiments, the sample classification and application server 220 further compares the sample's metadata with the metadata associated with the training images.

Process 900 also includes classifying the sample based on a closest match between the stored training images and the sample data (step 930). For example, as described above with respect to the sample classification module 730, the sample classification and application server 220 classifies the sample by based on the comparing (from step 920). More specifically, if a contaminant is present in the sample (e.g., when the dynamic speckle spectrum of the sample shows a relatively high degree of activity), the sample classification and application server 220 classifies the contaminant present in the sample. In embodiments, the sample classification and application server 220 determines the classification of the contaminant by matching the dynamic speckle spectrum data and metadata with the closest sample classification image and associated metadata set.

Process 900 also includes selecting and executing an instruction based on the sample classification (step 940). For example, as described above with respect to the instruction selection criteria repository 740 and the instruction execution module 750, the sample classification and application server 220 selects instruction to execute based on the classification of the sample/contaminant (e.g., as determined by the sample classification module 730) and the criteria stored by the instruction selection criteria repository 740 (e.g., an instruction to output information regarding the classification of the contaminant present in the sample, control treatment operations of a water or air supply controlled by an IoT device 215, provide an alert regarding the sample, generate a report regarding a contaminant present in the sample, schedule an appointment with a medical provider, executing a smart contract, etc.). Once the instruction is selected, the sample classification and application server 220 executes the selected instruction.

Process 900 further includes storing information regarding the classified sample in a data repository (step 950). For example, as described above with respect to the classification images and metadata repository updating module 760, the sample classification and application server 220 stores information regarding the classified sample in a data repository to aid in future classifications. As described herein, the dynamic speckle spectrum of a contaminant may evolve or change over time, and the sample classification and application server 220 tracks these changes by storing information regarding classified samples, such as the sample's dynamic speckle spectrum. That is, each time a sample is classified (e.g., in accordance with steps 910-940), the details of that sample (e.g., the sample's dynamic speckle spectrum) and the details of a contaminant present in the sample are stored. Thus, as the contaminant evolves, slight deviations can be detected between the dynamic speckle spectrum of the contaminant from a current sample, and the stored dynamic speckle spectrum of the contaminant.

Process 900 also includes updating training images repository based on previous classifications (step 960). For example, as described above with respect to the classification images and metadata repository updating module 760, the sample classification and application server 220 updates training images within the sample classification images and metadata repository 720 by tracking deviations in dynamic speckle spectrum images from previous classifications and updating the sample classification images and metadata repository 720 to update the training images as the dynamic speckle spectrum of the contaminant evolves. In this way, the sample classification and application server 220 implements machine learning techniques to update the training images such that classifying future samples is accurate as the dynamic speckle spectrum of a contaminant evolves. In embodiments, the sample classification and application server 220 adds to the training images stored in the sample classification images and metadata repository 720. For example, the sample classification and application server 220 saves the dynamic speckle spectrum images of samples having a same classification of contaminant so that those dynamic speckle spectrum images can later be used as training images for classifying future samples.

In embodiments, aspects of the present invention include a system having a sampling apparatus 210 and a remote server (e.g., a sample classification and application server 220). In embodiments, both the sampling apparatus 210 and the remote server are associated with a single entity. In an alternative embodiment, the sampling apparatus 210 and the remote server are associated with separate entities. In embodiments, the remote server receives dynamic speckle spectrum information of a sample from the sampling apparatus 210 and provides classification information of the sample as a service.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
receiving, by a computing device, data corresponding to a dynamic speckle spectrum image associated with a biological sample;
comparing, by the computing device, the dynamic speckle spectrum image with a plurality of training images;
classifying, by the computing device, a contaminant present in the biological sample, based on the comparing; and
executing, by the computing device, an instruction based on the classifying the contaminant,
further comprising receiving metadata associated with the biological sample, wherein the classifying the contaminant is further based on the metadata,
wherein the classifying compromises matching the dynamic speckle spectrum image and the metadata with a closet one of the plurality of training images and an associated metadata set.

2. The computer-implemented method of claim 1, further comprising building a repository of the plurality of training images to be used for the classifying, the building the repository comprising:
receiving respective dynamic speckle spectrum images of samples having known contaminants; and
storing information associating the respective dynamic speckle spectrum images with corresponding known contaminants.

3. The computer-implemented method of claim 2, further comprising storing the dynamic speckle spectrum image of the biological sample and information regarding the classification of the contaminant present in the biological sample in the repository to aid in classification of future biological samples.

4. The computer-implemented method of claim 1, wherein the biological sample is a fluid.

5. The computer-implemented method of claim 1, further comprising selecting the instruction from a plurality of instructions, based on the classification of the contaminant.

6. The computer-implemented method of claim 1, wherein the instruction includes at least one selected from the group consisting of:
controlling the operations of a treatment device;
providing an alert having information regarding the contaminant;
outputting information regarding the classification of the contaminant;
executing a smart contract; and
scheduling an appointment with a medical provider.

7. A computer-implemented method comprising:
storing, by a computing device, a plurality of training images in a blockchain;
storing, by the computing device, metadata associated with the plurality of training images in the blockchain;
receiving, by the computing device, data corresponding to a dynamic speckle spectrum image associated with a biological sample;
comparing, by the computing device, the dynamic speckle spectrum image with the plurality of training images;
classifying, by the computing device, a contaminant present in the biological sample, based on the comparing; and
executing, by the computing device, an instruction based on the classifying the contaminant.

8. The computer-implemented method of claim 1, wherein the data corresponding to the dynamic speckle spectrum image is received from a portable sampling apparatus.

9. The computer-implemented method of claim 1, wherein a service provider at least one of creates, maintains, deploys and supports the computing device.

10. The computer-implemented method of claim 1, wherein the receiving the data corresponding to the dynamic speckle spectrum image, the comparing the dynamic speckle spectrum image, and the classifying the contaminant are provided by a service provider on a subscription, advertising, and/or fee basis.

11. The computer-implemented method of claim 1, wherein the computing device includes software provided as a service in a cloud environment.

12. The computer-implemented method of claim 1, further comprising deploying a system, wherein the deploying the system comprises providing a computer infrastructure operable to perform the receiving the data corresponding to the dynamic speckle spectrum image, the comparing the dynamic speckle spectrum image, and the classifying the contaminant.

13. A computer program product comprising a computer readable storage medium having program instructions embodied therewith, the program instructions executable by a sampling device to cause the computing device to:
perform a speckle analysis on a biological sample by passing a laser through the biological sample and detecting a dynamic speckle pattern using a photodiode array, wherein the photodiode array takes a composite of plural images in a time domain to produce the dynamic speckle pattern; and
provide data from the speckle analysis to a server device to cause the server device to:
classify a contaminant present within the biological sample by comparing a dynamic speckle spectrum image associated with the speckle analysis with a plurality of training images, and
execute an instruction based on the classifying the contaminant.

14. The computer program product of claim 13, further comprising providing metadata associated with the biological sample to cause the server device to classify the contaminant further based on the metadata.

15. The computer program product of claim 13, further comprising providing data for respective dynamic speckle spectrum images of samples having known contaminants to cause the server device to store information associating the respective dynamic speckle spectrum images with corresponding known contaminants for classifying the biological sample.

16. The computer program product of claim 13, wherein the biological sample is a fluid.

17. The computer program product of claim 13, wherein data corresponding to the plurality of training images is stored in a blockchain and the information regarding the classification of the contaminant is stored in the blockchain.

18. The computer program product of claim 13, wherein the providing data from the speckle analysis to the server device to causes the server device to filter the data from the speckle analysis using a Fast Fourier Transforms (FFT).

19. The computer-implemented method of claim 1, wherein the metadata is received from one or more Intent of Things (IoT) devices.

20. The computer-implemented method of claim 1, further comprising:
- tracking deviations in dynamic speckle spectrum images from previous classifications; and
- updating the training images, based on the tracking, as the dynamic speckle spectrum of the contaminant evolves.

\* \* \* \* \*